United States Patent [19]

Giuliani et al.

[11] Patent Number: 5,263,218

[45] Date of Patent: Nov. 23, 1993

[54] VIBRATING TOOTHBRUSH USING A MAGNETIC DRIVER

[75] Inventors: David Giuliani, Mercer Island; Roy W. Martin, Redmond; Rodger H. Rosenbaum, Seattle, all of Wash.

[73] Assignee: GEMtech, Mercer Island, Wash.

[21] Appl. No.: 23,344

[22] Filed: Feb. 25, 1993

Related U.S. Application Data

[62] Division of Ser. No. 672,344, Mar. 21, 1991, Pat. No. 5,189,751.

[51] Int. Cl.⁵ .......................... A61C 17/34; B08B 1/00
[52] U.S. Cl. ........................ 15/22.1; 310/29; 310/36; 318/119
[58] Field of Search ........... 15/22.1, 22.2, 22.4; 310/10, 20, 27, 36, 37, 39, 29; 464/29; 318/119, 129; 30/45

[56] References Cited

U.S. PATENT DOCUMENTS

| | | | |
|---|---|---|---|
| 1,832,519 | 11/1931 | Wheat et al. | 15/22.1 |
| 2,044,863 | 6/1936 | Sticht | 15/22.1 |
| 2,246,523 | 6/1941 | Kulik | 15/22.1 |
| 2,278,365 | 3/1942 | Daniels | 15/22.1 |
| 2,709,227 | 5/1955 | Foley et al. | 15/22.1 |
| 2,734,139 | 2/1956 | Murphy | 310/29 |
| 2,878,499 | 3/1959 | Pressman | 15/22.1 |
| 2,917,758 | 12/1959 | Held | 15/22.1 |
| 2,977,614 | 4/1961 | Demanuele | 15/22.1 |
| 3,159,859 | 12/1964 | Rasmussen | 15/22.1 |
| 3,493,793 | 2/1970 | Niemela | 310/37 |
| 3,500,080 | 3/1970 | Bey | 310/36 |
| 3,535,726 | 10/1970 | Sawyer | 15/22.1 |
| 3,538,359 | 11/1970 | Barowski | 15/22.1 |
| 4,787,847 | 11/1988 | marti et al. | 15/22.2 |

FOREIGN PATENT DOCUMENTS

609238  2/1979  Switzerland ............ 15/22.1

*Primary Examiner*—Edward L. Roberts
*Attorney, Agent, or Firm*—Jensen & Puntigam

[57] ABSTRACT

A toothbrush which includes a toothbrush body (12) and a lever arm (14) having toothbrush bristles (18) at one end thereof. The lever arm (14) is mounted for pivotal movement at a pivot member (16) which is in the vicinity of the other end of the lever arm (14). In one embodiment, a pair of permanent magnets (44, 46) are provided at the other end of the lever arm (14), positioned side-by-side with opposite polarities. An electromagnet (24) is provided to the rear of the lever arm (14). The electromagnet (24) includes an E-core having top, bottom and center legs (30, 31, 33) with a coil (36) wound around its center leg (33) which receives an alternating current driving signal from an oscillator/battery section (38). The frequency of operation is in the range of 150-400 Hz. The action of the alternating current in the electromagnet (24) causes the lever arm (14) to move about the pivot member (16), first in one direction and then in an opposing direction to provide the desired vibrating effect.

20 Claims, 4 Drawing Sheets

FIG. 10

VIBRATING TOOTHBRUSH USING A MAGNETIC DRIVER

This is a divisional of application Ser. No. 672,844, filed on Mar. 21, 1991, now U.S. Pat. No. 5,189,751.

TECHNICAL FIELD

This invention relates generally to dental hygiene devices and more specifically concerns a vibrating toothbrush which includes a magnetic driver.

BACKGROUND ART

Power-driven toothbrushes are generally well-known. Through the use of various driving mechanisms, the bristles vibrate, oscillate or rotate so as to remove dental plaque thoroughly and quickly. The abrasion of gum tissue by use of excessive force (brush action), however, has been recognized to be a possible risk of power toothbrushes, and accordingly, many current power toothbrushes are designed to minimize abrasion of gum tissue as much as possible.

In addition to the use of such a toothbrush to remove dental plaque, power toothbrushes have been designed which produce an acoustical cleaning effect, which increases general performance as well as cleaning the subgingival area of the teeth between the teeth and gums and demobilizing the motile bacteria therein. The acoustic phenomenon is achieved by streaming/cavitation of fluid in the mouth, either saliva or other fluid. Examples of patents which teach a toothbrush producing the acoustic effect through sufficient bristle vibration include U.S. Pat. Nos. 3,924,335 and 3,809,977 to Balamuth, and U.S. Pat. No. 4,787,847 to Martin. Adequate cavitation to produce an acoustic effect requires a minimum instantaneous pressure change in the cavitational fluid in the mouth, which in turn requires a minimum instantaneous velocity of the bristles.

Numerous drive system designs for such a toothbrush have been designed. One example is shown in U.S. Pat. No. 3,535,218 and 3,676,218 to Sawyer, which utilizes a cantilevered beam arrangement with a fixed displacement driving mechanism, i.e. a motor crank and actuator arrangement.. The beam is designed to operate as a spring element, but is positioned between the driver and the load, resulting in high source impedance and poor resistance to damping. In U.S. Pat. No. 4,175,299 by Teague, et al, an orbital brush arrangement is shown, using a lever which operates through a pivot which in turn converts the drive on one end of the lever to orbital action on the other end of the lever. U.S. Pat. No. 4,149,291 to Stoltz is an example of a brush having an elliptical motion which uses a crank-like configuration operating through a pivot to convert the rotation of a motor to the elliptical movement of the brushhead, while U.S. Pat. No. 3,978,852 to Annoni teaches a pivot arrangement in which the brush moves in a single plane.

All of these mechanically linked drive systems suffer from several disadvantages. Friction due to several surface-to-surface contact points in the various linkage arrangements produce significant power loss and result in rather low power efficiency for the various toothbrushes. While these disadvantages are not as significant when the toothbrush is powered from a 120-volt wall source, they do significantly limit the possibility of a battery-powered appliance capable of both scrubbing and acoustical cleaning. As a result, practical implementation of a battery-powered acoustic toothbrush has not occurred.

A magnetic drive system offers promise of relief from such power constraints. One of the significant advantages of a magnetic drive system is that the drive unit may be physically separate from the lever arm and hence the brushhead, which is at the far end thereof. Hence, any power loss due to mechanical linkages can be avoided. Examples of magnetically driven toothbrushes and/or similar appliances include U.S. Pat. No. 3,500,080 to Bey, which teaches a toothbrush driver comprising a combination of a permanent magnet and an electromagnet to drive a vibrating lever arm member and U.S. Pat. No. 2,734,139 to Murphy which teaches an electric eraser which includes an E core electromagnet having coils around the center leg thereof. Other patents which specifically teach a toothbrush using magnetic drive principles include U.S. Pat. No. 3,538,359 to Karl-Heinz Barowski, U.S. Pat. No. 2,977,614 to Demanuel, and U.S. Pat. No. 2,278,365 to Daniels. Further, Swiss patent No. 609238 specifically teaches a vibrating toothbrush which would appear to have an ultrasonic cleaning capability and which includes an ancillary magnetic drive system for indicating an excess load condition on the brushhead. The magnetic drive system includes a non-resonating arm and a limit on arm travel such that the system becomes non-operational at relatively small pressures.

Due to the overall design of such units, they are typically not very efficient and the use of battery power for such devices is not practical. A substantial amount of energy is usually lost in the form of air gap flux. Further the units are typically appropriate only for relatively low frequency vibration due to the high mass of the vibrating member and/or the drive system. Low frequency vibration makes fluid cavitation/streaming questionable for such units.

Hence, there remains a continuing need for an efficient, practical, power vibrating toothbrush which is capable of producing sufficient acoustical pressure to produce reliable cavitation and streaming as well as simultaneously scrubbing the teeth. It is desirable, furthermore, that the toothbrush be capable of operating from a battery. It is also desirable that the toothbrush vibrate with relatively minimal amplitude when unloaded, with an increase in amplitude when the bristles are loaded. It is further desirable to minimize the number of moving parts in such a toothbrush, including avoiding mechanical linkages and complex sealing arrangements. It is still further desirable to prevent the user from applying force to the brush beyond a pre-established limit, in order to avoid excess abrasion and to allow bristles to vibrate in an acoustically effective manner.

DISCLOSURE OF THE INVENTION

Accordingly, in one embodiment, the present invention is a vibrating toothbrush which includes a magnetic driver, comprising a toothbrush body, a lever arm which has toothbrush bristles at one end thereof, means for mounting the lever arm for vibrating action, and electromagnetic means for driving the lever arm about the mounting means, wherein there is no direct mechanical connection between the driving means and the lever arm, and wherein the electromagnetic means drives the lever arm at an operating frequency which is approximately equal to the natural mechanical resonant frequency of the combination of the lever arm and the mounting means.

Another embodiment includes a means for driving the lever arm, not necessarily electromagnetic, at an operating frequency which is different than the resonant frequency of the combination of the lever arm and the mounting means by a small selected amount, such that the amplitude of vibration of the lever arm increases when the lever arm is in a loaded condition as opposed to an unloaded condition.

In still another embodiment, the electromagnetic means for driving the lever arm includes permanent magnet means located on the lever arm in the vicinity of the other end thereof, and further includes an electromagnet, wherein the electromagnet includes a first inductance to which a driving signal is applied and an energy recovery circuit for storing reactive energy which comprises a series connection of a second inductance and a capacitor, wherein the first and second inductances are arranged such that energy from the driving signal through the first inductance is coupled into the second inductance, and wherein the second inductance cooperates with the permanent magnet means to drive said lever arm.

Still further, the present invention is a vibrating toothbrush having a magnetic driver which includes a head portion which in turn includes a head body, a lever arm having permanent magnet means located at one end thereof and means for mounting the lever arm for vibrating action, a toothbrush element which includes bristles, the toothbrush element being removable relative to the other end of the lever arm, and driver means which includes a driver body, an electromagnet and signal means for driving the electromagnet at an operating frequency, wherein the head portion is readily removable relative to the driver portion.

BEST MODE FOR CARRYING OUT THE INVENTION

Figure 1:
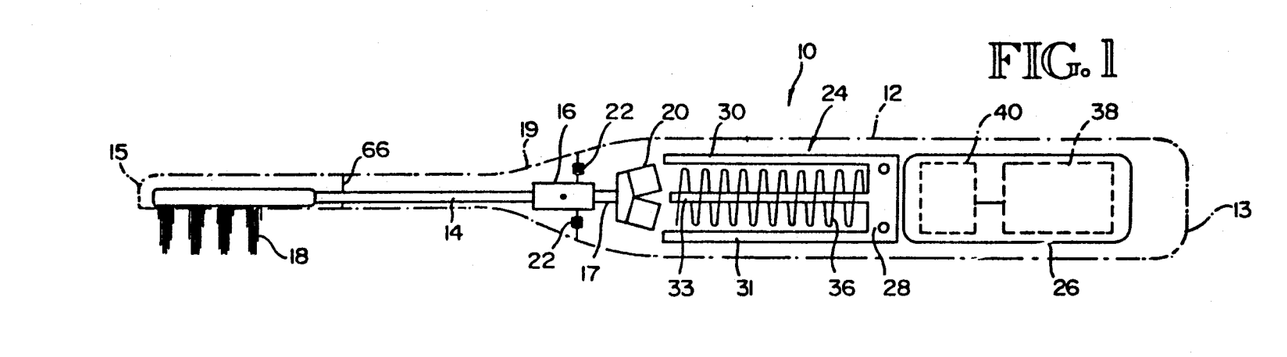
FIG. 1 is a cross-sectional view showing the toothbrush of the present invention.
Figure 3:
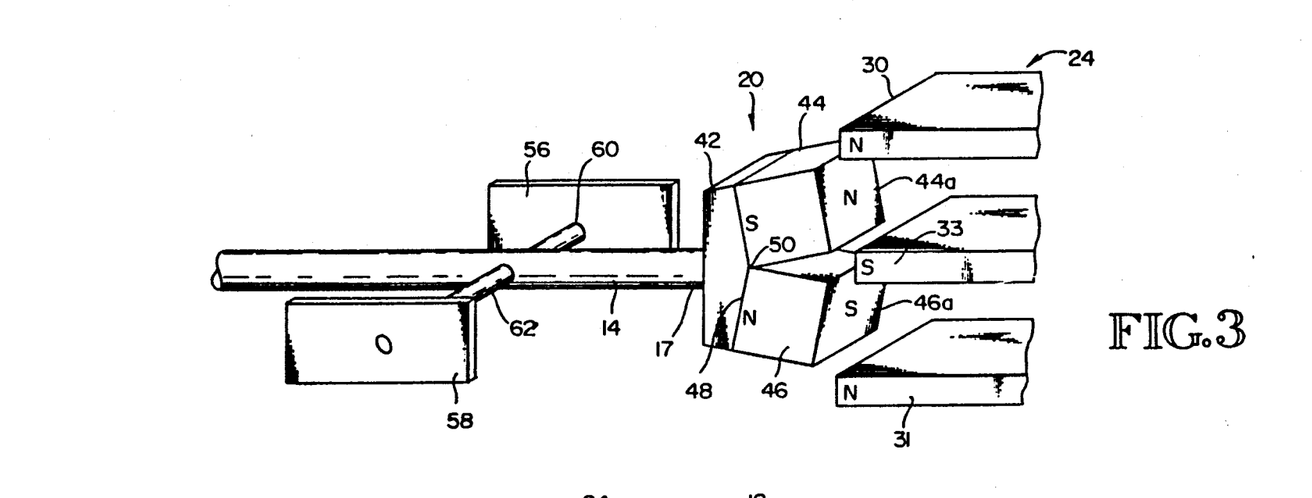
FIG. 3 is an elevational view showing a portion of the toothbrush of FIG. 1.

FIGS. 1 and 3 show one embodiment of the battery-powered, magnetically driven toothbrush of the present invention. The toothbrush, shown generally at 10 in FIG. 1, includes an elongated hollow case 12 within which are the other portions of the toothbrush, including a battery. The case 12 is generally circular in cross section, having a diameter of approximately 1.2 inches for approximately, half of its length from the rear end 13 thereof, narrowing down to a relatively small diameter of approximately 0.37 inches over the remainder of its length to the front end 15 thereof. This arrangement provides an attractive package for the toothbrush of the present invention while also being convenient for the user to operate.

Within case 12 is an elongated lever arm 14 which is mounted on a pivot member 16 which permits vibration of the lever arm in one plane (vertically in FIG. 1). While FIG. 1 is arranged to show vertical movement of the lever arm and hence the brush, for ease of illustration, it should be understood that the apparatus could be arranged so that the lever arm and the brush move in a horizontal (side-to-side) direction as well, or the brush can be positioned at specific angles to provide movement in an angled plane. The pivot member 16 is located near one end 17 of the lever arm 14 in the embodiment shown, but it should be understood that the pivot member could be positioned at other points between the two ends of the lever arm. The pivot member is mounted to case 12 in the area 19 where the diameter of the case 12 narrows down. At the other end 14 of the lever arm 14 is a brush 18 which is arranged to be readily removable relative to the lever arm 14. The brush 18 extends through an opening in the case 12 near the front end 15 thereof.

It should be understood, as explained in more detail below, that the lever arm 14 may be mounted relative to the pivot member and the case 12 in such a manner and may be otherwise arranged in such a manner that the lever arm 14, either by itself, or in combination with the pivot member 16 and/or a portion of the case, may be conveniently removable from the remainder of the toothbrush apparatus. A spring element 22 is connected between the lever arm 14 and the case 12, typically at the pivot member 16 or in the vicinity thereof, to bias the lever arm 14 in a central position, as shown in FIG. 1, between its two vertical extremes of vibrating movement.

At the rear end of lever arm 14 is a permanent magnet assembly 20 which is shown in detail in FIG. 3 and discussed below. The toothbrush 10 also includes an electromagnet 24 and a battery/oscillator section 26. The electromagnet 24 comprises in its simplest form an E-shaped core 28 having upper and lower legs 30 and 31 and a center leg 33. A coil 36 is wound around the center leg 33. A conventional battery 38 provides power to an oscillator 40 which produces an operating signal having a selected operating frequency, the operating signal being applied to coil 36. In one embodiment, the operating frequency is selected to be relatively near or at the mechanical resonance of the combined lever arm and pivot member mechanical system, so that the drive system can be appropriately described as a resonant magnetic driver. In the embodiment shown, the range of the operating frequency is 150 to 400 Hz, at amplitudes (loaded) of 0.07 to 0.15 inches. This combination supplies a sufficiently high amplitude-frequency product to produce required cavitation and streaming effects in addition to effective scrubbing, yet be low enough in frequency as to not sound irritating to the user.

FIG. 3 shows the permanent magnet assembly 20 at the rear end 17 of the lever arm 14 and the operating relationship between the permanent magnet assembly 20 and the electromagnet 24. In the embodiment shown, an iron backing member 42 is secured to the rear end 17 of lever arm 14. Two individual permanent magnet elements 44 and 46 are secured to the iron backing member 42, extending toward electromagnet 24. The rear face 48 of the iron backing member 42 angles slightly forwardly from a center line 50 to the opposing edges thereof. The permanent magnet elements 44 and 46 thus tend to diverge in the direction of electromagnet 24, as seen in FIG. 3, such that at the closest point to the electromagnet, they are separated by a gap of approximately 0.05 inches. While the rear faces 44a, 44b of permanent magnets 44 are thus shown to be angled slightly forwardly, it should be understood that the two magnets could be positioned together, with the rear faces 44a, 46a of the permanent magnets being in the same plane. The arrangement illustrated, however, is somewhat more efficient. Permanent magnet element 44 is positioned such that its south pole is adjacent the iron backing member 42 while its north pole faces the electromagnet. Permanent magnet element 46 is oppositely positioned, with its north pole being adjacent the iron backing member 42 and its south pole facing electromagnet 24.

In the embodiment shown, there is no physical contact necessary between the lever arm and the electromagnet and as a result, the power handle can be sealed with a solid continuous wall between the electromagnet and the lever arm.

The permanent magnet elements 44 and 46, in one embodiment, are rare earth magnets, such as Neodymium-Iron-Boron or Samarium Cobalt, due to their excellent energy density product. Ne-B-Fe magnets are a particularly good choice because of their decreasing cost and the fact that they generate a strong bias field in the working gap, i.e. approximately 8,500 Gauss. It should be understood, however, that permanent magnets of lower energy density such as Alnico can also be used.

When the driving signal has a first polarity, the upper and lower legs 30, 31 of the electromagnet 24 have north polarities, while the center leg 33 has a south polarity. During the other polarity of the driving signal, the relative polarities of the electromagnet are opposite, i.e. the upper and lower legs have south polarities, while the center leg has a north polarity. There is thus an alternating polarity at the tips of the three legs of the electromagnetic as the driving signal applied to the coil 36 alternates in polarity. The upper and lower legs of the electromagnet extend slightly forwardly of center leg 33, to "match" the angled faces of the permanent magnets. If the faces of the permanent magnets are in one plane, the tips of the legs of the electromagnet will also typically be in one plane.

The flux from the tips of the legs 30, 31, 33 of the electromagnet 24 flows through the gap between adjacent legs. The flux in the gap creates an instantaneous combination of retraction and repulsion forces on the permanent magnet elements 44 and 46 which in turn create a torque on the lever arm 14 about the pivot member 16. This ultimately results in a vertical (up-/down) movement of the brush at the operating frequency of the oscillator for the embodiment of FIG. 1, or other periodic reversing action for other embodiments.

When the upper and lower legs are both north polarity and the center leg is south polarity, there will result a repulsion between the upper leg 30 and the upper permanent magnet 44 as well as repulsion between center leg 33 and lower permanent magnet element 46. These repulsion forces tend to force the lever arm to move in a clockwise direction about the pivot member 16. Attraction will occur between the upper permanent magnet element 44 and the center leg 33 as well as between the lower permanent magnet element 46 and the lower leg 31 of the electromagnet. The attraction forces also tend to force the lever arm 14 in a clockwise direction.

When the upper and lower legs are south polarity and the center leg is north polarity, repulsion and attraction forces similarly occur, but cooperate to produce a counter-clockwise movement for the lever arm 14. Thus, the lever arm 14 moves alternately clockwise and counter-clockwise through an angle of approximately ±3° the embodiment shown, with spring member 22 tending to bias the lever arm in a center position. It should be understood that the angle of movement can be varied somewhat. The force exerted on the lever arm is relatively independent of its angular position, thus producing an approximately constant force drive. In such a driver, the angular excursion increases with increasing work, thereby facilitating the desired characteristic of the amplitude of movement of the lever arm increasing with load. The driving signal is produced by conventional circuitry, including an oscillator and a source of power, such as a battery. The required switching may be accomplished with several different elements, including bipolar transistors, FETs or even relays.

FIG. 3 also shows a particular pivot member arrangement. In this arrangement, the pivot member includes two side support elements 56 and 58. Side support elements 56 and 58 are small, relatively thin blocks of material which are fastened to the case 12. Extending inwardly from the side support elements 56 and 58 are two torsion arms 60 and 62. Torsion arms 60 and 62 could be integral with the side supports 56 and 58 or securely attached thereto. The torsion arms 60 and 62 in turn are bonded to or are an integral part of lever arm 14. In one particular embodiment, lever arm 14, side support elements 56 and 58 and torsion arms 60 and 62 are made from one molded plastic assembly. In another alternative embodiment, torsion arms 60 and 62 and side support elements 56 and 58 could be prefabricated from spring steel, with the torsion arms then secured to lever arm 14. In a specific example, torsion arms of hardened steel material, such as music wire, with a length of 0.25 inches and a diameter of 0.078 inches, will be suitable for a resonant frequency of approximately 250 Hz.

In operation, the torsion arms 60, 62 will tend to bias the lever arm 14 in its center position, i.e. the force exerted on the torsion arms 60 and 62 by a movement of the lever arm in one direction or the other will tend to cause the lever arm to return to its center position when the force is removed. This restoring action is due to the spring action of the torsion arms and therefore the spring factor of the torsion arms is a key part of the mechanical resonance of the combined brush and lever assembly. The torsion arms permit rotation of the lever arm in the plane of their length (longitudinal plane) only, tending to prevent, for instance, both axial and vertical travel by the lever arm, as well as rotation about any other axis. The torsion arm pivot member has the further advantage of having no frictional moving parts, thus resulting in a relatively low loss vibrational mechanism. Additionally, part tolerance is not a major concern.

Figure 4:
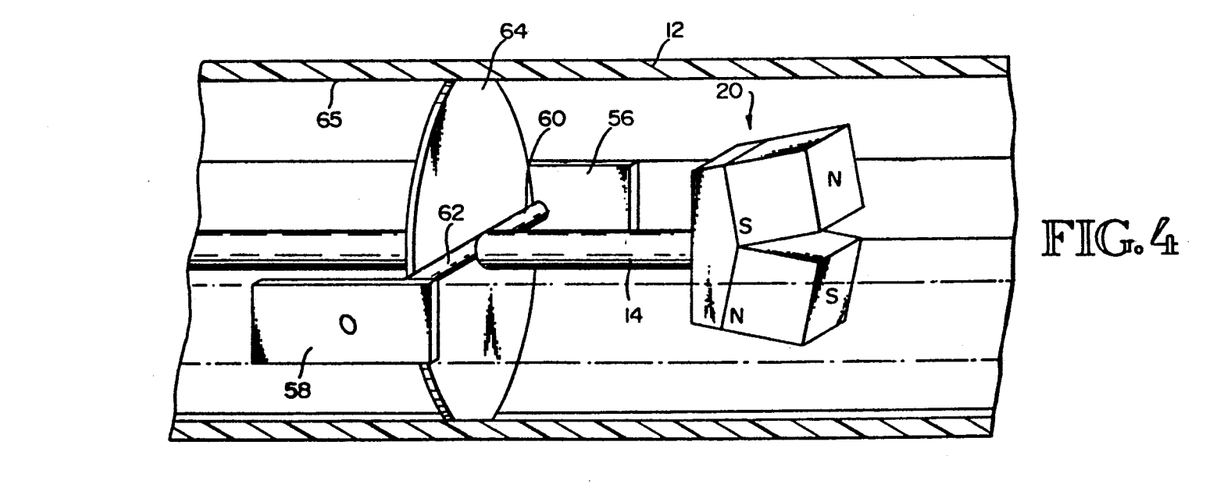
FIG. 4 is an elevational view showing a specific feature of the present invention.

Referring now to FIG. 4, a diaphragm 64 may be provided in the toothbrush apparatus which is securely attached to or an integral part of the torsion arm assembly, extending outwardly to the interior surface 65 of the case 12. Diaphragm 64 provides a convenient seal for the toothbrush in the vicinity of the pivot member. Diaphragm 64 could be made integral with the pivot member (i.e. the torsion arm assembly in FIG. 4) or it could be located separate from the torsion arm assembly, but usually in the immediate vicinity thereof.

Further, a seal or diaphragm could be provided remote from the pivot member, such as element 66 in FIG. 1. In such a case, seal 66 is flexible, and extends from the lever arm 14 to the interior boundary of the case. The seal 66 is designed to flex with the movement of the lever arm without disturbing the sealing function. The use of a seal near the brush end of the lever arm 14 prevents liquid from the brush area moving back into the toothbrush apparatus. A seal 66 could also be provided in the same toothbrush apparatus with diaphragm element 64.

The above-described seals (diaphragm) are simple and inexpensive to implement and eliminate the inefficient and costly seals of other toothbrush devices where there is a rotational or translational movement component to the vibration of the lever arm of the device.

Figure 5:
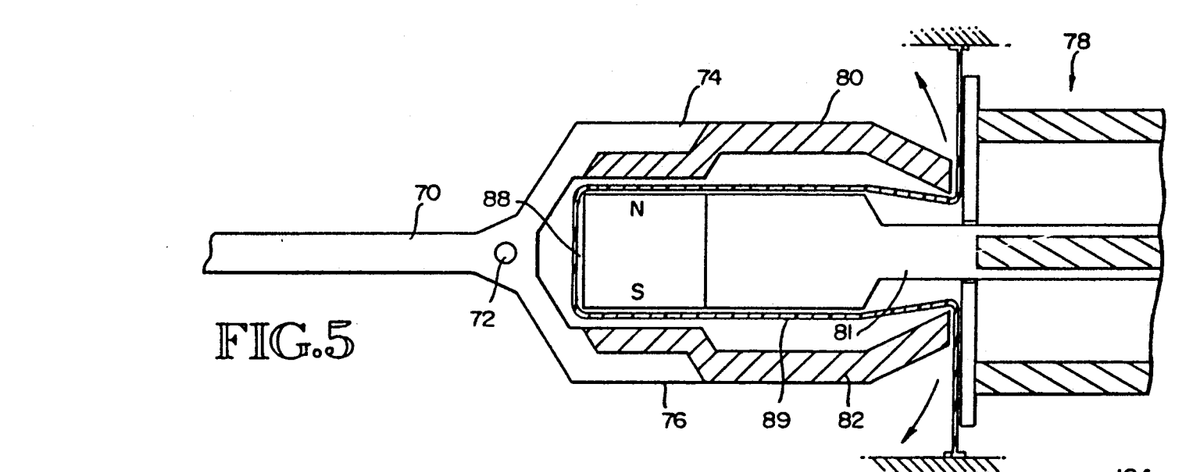
FIG. 5 is a simplified elevational view showing a portion of another embodiment of the present invention.

In the embodiment of FIG. 5, the bias flux necessary for driving the lever arm 70 is produced with the permanent magnet 88 being fixedly positioned within the apparatus instead of being positioned directly on the lever arm. This results in a reduction of the overall cost of the lever arm. The lever arm 70 is pivoted at 72, in a manner similar to that shown and described above. The lever arm branches outwardly and rearwardly from the pivot point 72 into two yoke arms 74 and 76, toward the electromagnet shown generally at 78. Rear portions 80 and 82, respectively, of the yoke arms 74 and 76 include ferromagnetic material, such as iron.

Positioned about the center leg of the electromagnet 78 is a fixed support member 81 which extends between the yoke arms 74 and 76, as shown in FIG. 5, and on the forward end of which is mounted a permanent magnet 88. Portions 80 and 82 operate to couple magnetic flux from the fixed permanent magnet 88 to the electromagnet 78. A seal 89 for the apparatus may be provided which extends from the interior surface of the case (not shown) between the yoke arms 74 and 76 and the permanent magnet 88. Thus, there results an effective internal seal between the two yoke arms 74 and 76 with their respective ferromagnetic portions 80 and 82 relative to the combination of the fixed permanent magnet 88 and the electromagnet 78.

The elements shown in the embodiment of FIG. 5 can be arranged to insure that the flux density in the gap between the ferromagnetic portions 80 and 82 and permanent magnet 88 is similar to that of the embodiment of FIG. 1.

One advantage of the arrangement of FIG. 5 is that the lever arm assembly, including the yoke arms 74 and 76, is inexpensive and therefore is practical to replace, although the permanent magnet 88 is typically more expensive than the permanent magnets in the embodiment of FIG. 1. Further, the moment of inertia of the lever arm assembly of FIG. 5 is typically less than the moment of inertia for the lever arm of the embodiment of FIG. 1, which in turn permits the use of a higher resonant frequency and/or results in a reduction in the amount of vibration coupled back into the toothbrush apparatus for the FIG. 5 embodiment.

Figure 6:
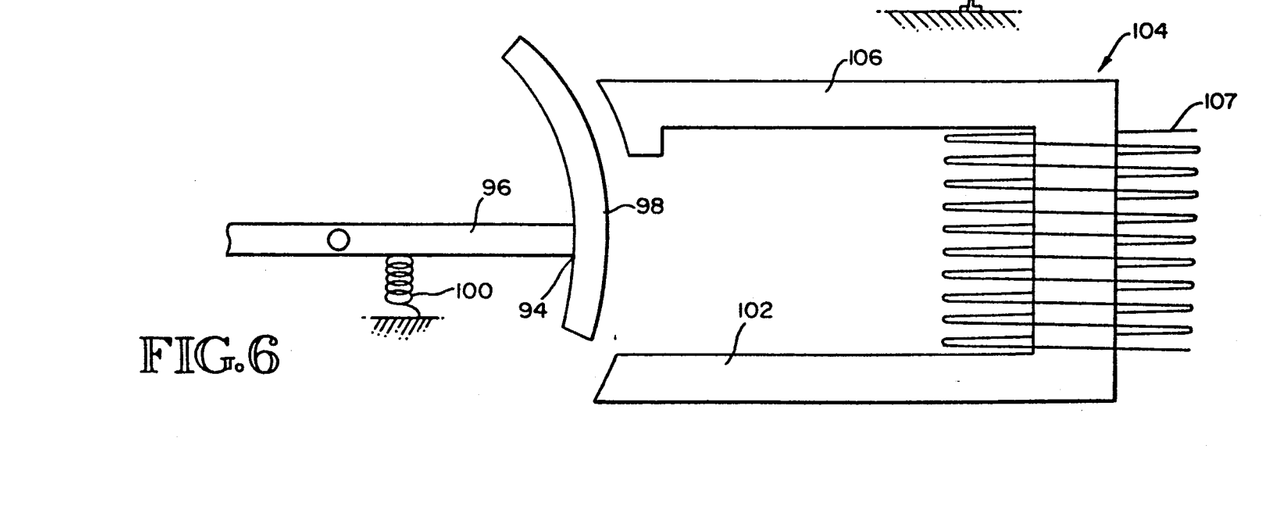
FIG. 6 is a simplified elevational view showing a portion of another embodiment of the present invention.

FIG. 6 shows another embodiment of the toothbrush apparatus of the present invention, involving a variable reluctance. The rear end 94 of lever arm 96 has attached to it an iron or steel curved member 98 which is typically approximately 0.7 inches long. The spring 100 tends to maintain the curved member 98 out of the gap between it and the lower leg 102 of the electromagnet 104. The reluctance between the upper leg 106 of electromagnet 104 and the curved member 98 is relatively low and remains constant with the normal rotational movement of the lever arm. The reluctance between the curved member 98 and lower leg 102 decreases when the lever arm 96 rotates counter clockwise against the action of the spring 100, during the time that the drive signal applied through coil 107 has the appropriate polarity. The arrangement of FIG. 6 is particularly useful when the lever arm is relatively long, so that the "throw distance", i.e. the movement of the brushhead end of the lever arm, is several times the gap length.

Figure 7:
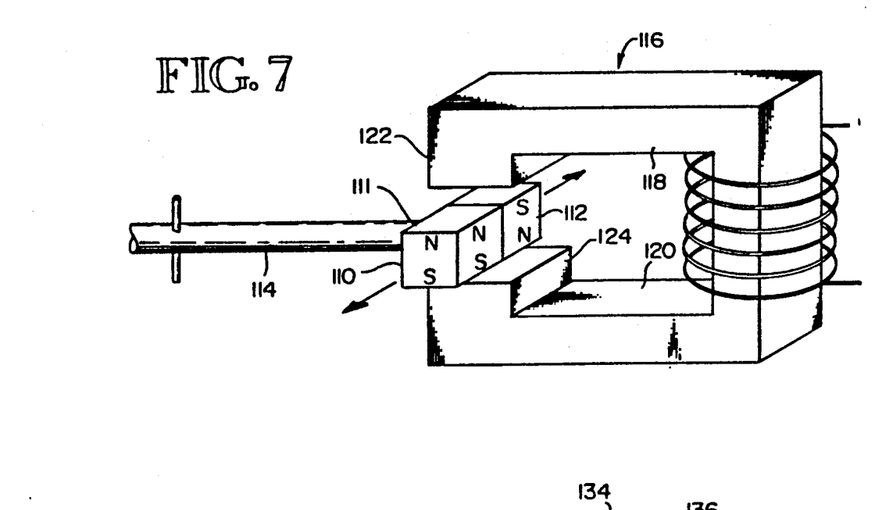
FIG. 7 is a simplified elevational view showing still another embodiment of the present invention.

FIG. 7 shows a still further embodiment of the present invention. In this case, the permanent magnets 110 and 112, on the rear end 111 of lever arm 114, are arranged relative to the electromagnet 116 so that the lever arm and hence the brush move sideways. The electromagnet 116 is generally U-shaped, having opposing upper and lower legs 118 and 120, with the end portions 122 and 124 of upper and lower legs 118 and 120, respectively, being at right angles to the remaining portions of the upper and lower legs and extending a short distance toward each other. Permanent magnets 110 and 112 are located in the gap between end portions 122 and 124. The permanent magnets 110 and 112 are arranged so that their respective poles face in opposite directions, toward the end portions 122 and 124 of legs 118, 120. In operation, during one half cycle of the driving signal, the poles of the electromagnet are biased so that one permanent magnet is repulsed by the poles and the other permanent magnet is attracted to them. The action is reversed during the other half cycle. The advantage of this particular design is that the gap between the permanent magnets 110 and 112 and the legs of the electromagnet is smaller (e.g. 0.02 inches) and remains constant.

Figures 8, 9:
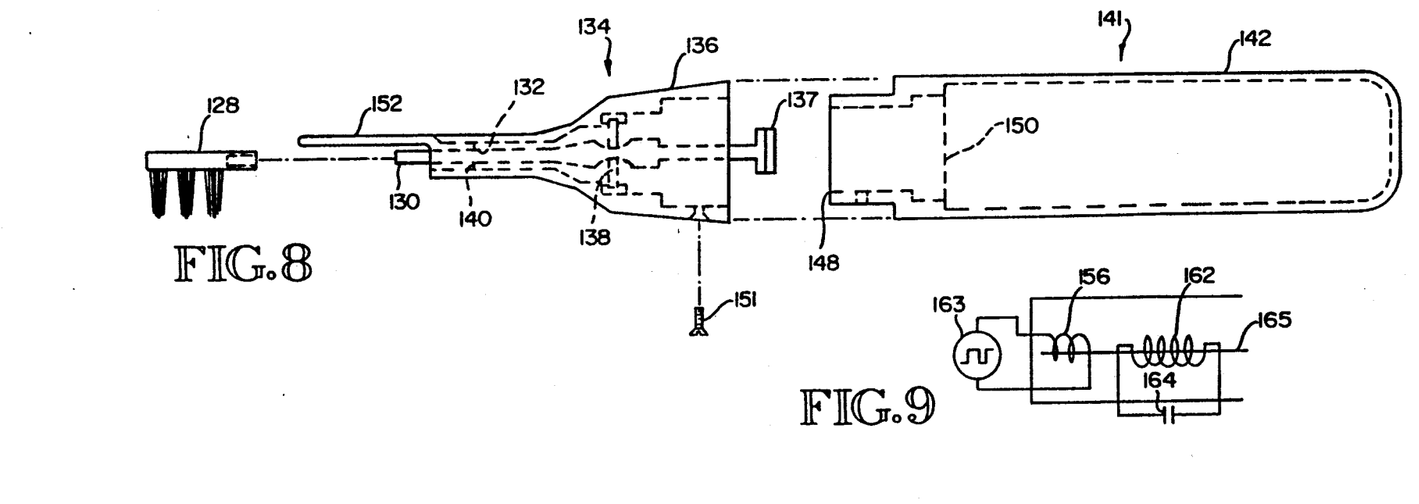
FIG. 8 is a simplified exploded view showing one embodiment of the mechanical arrangement of the toothbrush of the present invention.
FIG. 9 is a diagram illustrating the energy storage feature of the present invention.

FIG. 8 shows one embodiment of an overall structural arrangement of the apparatus of the present invention. In this particular arrangement, the toothbrush apparatus is divided into three readily separable sections. The first section is the brush 128, which is readily removable from the forward end 130 of lever arm 132. The second section is a head member shown generally at 134 which includes a case portion 136 which in turn includes a shield element 152 for brush 128, a lever arm 132 and a torsion arm pivot member 138 As explained above, the pivot member 138 and lever arm 132 may be an integral unit. The lever arm is pivoted for side-to-side brush movement. The lever arm extends a selected distance to the rear of pivot member 138, as shown. At the rear end of the lever arm are two permanent magnets 137-137, arranged in a side-by-side arrangement (into the page). A seal 140 may also be provided around the lever arm close to the brush 128, as explained above. The third section is a driver 141 which includes a case portion 142, which in turn contains electromagnet, battery and oscillator portions (not shown). Near the forward end 148 of driver section 141 is a wall 150 which completely seals the driver section from the remainder of the toothbrush.

The head section 134 is configured to be readily removable from the driver section 141 by means of screw threads, snap connections or other similar elements, such as a screw 151 shown in FIG. 8. Such an arrangement permits the use of several different head sections with a single driver section, without any complex sealing mechanisms between the two sections.

Figure 2:
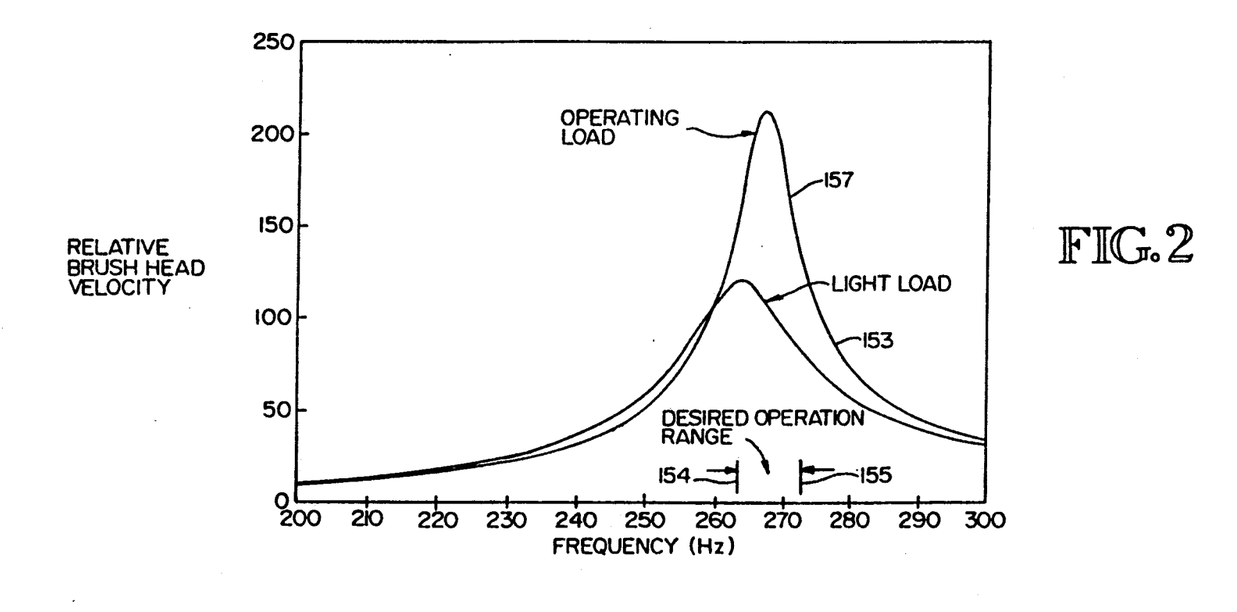
FIG. 2 is an amplitude versus frequency diagram illustrating one feature of the present invention.

FIG. 2 illustrates another significant feature of the present invention, in which the load on the bristles controls important performance characteristics—brushhead velocity and power delivery to the load, when the operating frequency is slightly different than the natural resonant frequency of the device, i.e. within a range of 5 Hz to 40 Hz, preferably approximately 15 Hz. FIG. 2 shows frequency of movement of the brushhead vs. velocity of the brushhead (shown in millimeters per second multiplied by a scaling factor for comparison purposes). Velocity of course has a direct relationship to amplitude. When in air (unloaded) or very lightly loaded the resonant properties are determined primarily by the inertia and compliance characteristics of the lever arm and pivot member. The "light load" brushhead velocity curve 153 is relatively low over the desired range of operating frequencies, indicated by lines 154–155, thereby minimizing noise and splatter.

Placing the bristles against the teeth and/or into the saliva and toothbrush fluid results in heavier damping of the bristle tips. This increased damping couples the compliance of the bristles into the resonant mechanical structure, with resulting changes in the velocity versus frequency characteristics. By selection of design parameters the velocity versus frequency response can be altered in magnitude, peak frequency, and bandwidth or "Q". For example, in FIG. 2, the "operating load" curve 157 shows that over the desired operating range the magnitude increases by about a factor of 2 over the light load case (curve 153). Additionally, the design can be tailored to supply maximum power to the load and a selected level of damping, by using complex conjugate impedance matching of the load to the lever arm output impedance. Specifically, the compliance of the bristles is used to effectively cancel the mass-like component of the output impedance above resonance, while the load damping matches the real component of the output impedance. This optimum damping can be set at relatively light loading forces (e.g. 100gms) to avoid excessive pressure on the gums and teeth.

The operating frequency can also be adjusted to control the supplied power level. As shown in FIG. 2, operating frequency can be increased by 5 Hz to reduce both the loaded and unloaded brushhead velocity by about a factor of 2.

Another feature utilizing resonant behavior of the device concerns quenching the brushhead velocity when force loading on the bristles exceeds a certain threshold. This damping is achieved when bristles are compressed onto the tooth surface, especially at an acute angle. Referring to FIG. 8, quenching at a level of excess loading can also be achieved by selecting the compliance of the lever arm 132, and the unloaded gap between the brushhead 128 and shield 152, so that this gap is eliminated (and contact occurs) at the maximum allowable force. This method works best in an embodiment employing side-to-side motion, as shown in FIG. 8. Use of a friction generating material such as rubber can provide a damping capability; use of one or more bumped surfaces can also supply an audio signal indicating excess force condition. This feedback facilitates training as well as guarding against excess force by reducing the power delivered.

In general, modifying resonant performance by use of varying bristle loading can supply several benefits in oral hygiene application: (1) minimum velocity when unloaded to reduce fluid and toothbrush splatter and noise; (2) maximum velocity when loaded to enhance cavitation and acoustical streaming in bristle regions still free to vibrate; (3) maximum power transfer to the bristle scrubbing action at typical usage damping, which can be set at relatively low pressures; and (4) limiting or quenching vibrational velocity when the brushhead is overdamped to minimize excess force being applied to the head. Different heads can be supplied with different bristle configurations, each optimized for specific applications.

Another feature of the present invention is shown is FIG. 9. As background, the arrangement of FIG. 1 includes a relatively large air gap, comprising the path from the electromagnet through one permanent magnet to the backing iron member and then through the permanent magnet to the center leg of the electromagnet. The relative permittivity of the permanent magnet is approximately zero, which contributes to a relatively high magnetic reluctance path. This large reluctance requires a correspondingly large instantaneous energy stored in the gap for a given instantaneous flux density, requiring a correspondingly large magnetomotive force. Additional magnetomotive force is required to support the leakage flux between and around the electromagnetic poles. The resulting reactive flux is thus many times higher than the flux required to supply power to the brush, especially when the brush is unloaded.

Although the embodiment of the present invention shown in FIG. 1 is a significant improvement over previous designs and permits the use of a battery for power, there is still a substantial amount of energy dissipated in the FIG. 1 device corresponding to the high values of magnetomotive force used. Specifically, this power is lost in dissipative elements, such as $I^2R$ losses in coils and switching circuits. In one example, for an operating magnetomotive force (MMF) of the circuit of FIG. 1, the impedance of the coil is 2.3 ohms (inductive reactance), 0.22 ohms resistance, while the resistance of the switching circuitry, in particular the transistor switches, is 0.3 ohms. The number of turns of the primary coil is 150. The current is approximately 1.6 amperes and the voltage 4.6 volts at a quiescent operating condition, for a power dissipation of 1.3 watts when the device is quiescent. This is a significant amount of power loss.

A significant reduction in energy lost is accomplished through the use of the energy storage circuit shown in FIG. 9. This circuit includes a primary coil 156, which is wound around the center leg 165 of the electromagnet and which is driven by an oscillator/battery combination 163. Also wound around the center leg 165 is a resonating coil 162 which is in series connection with a capacitor 164. The capacitor 164 is typically quite small, i.e approximately microfarad. The number of turns in the primary coil 156 in the embodiment shown is approximately 45, while the number of turns in the resonating coil 162 is approximately 3000. In this arrangement, the primary coil 156 receives power from the battery required to support the losses associated with the actual work performed by the device, while the combination of the resonating coil 162 and capacitor 164 stores and returns reactive energy from the magnetic core of the electromagnet.

In the above example, for a MMF (magnetomotive force) of 150 ampere-turns, the resistance of the resonating coil is 100 ohms, the resistance of the primary coil is 0.3 ohms, the current in the primary coil is 0.2 amps unloaded and 1.0 amps loaded while the primary coil voltage is 1.5 volts, resulting in a power loss of 0.25 watts when the device is in a quiescent condition. Under such operating conditions, the device can be powered readily with two NiCad cells. It has been determined that such a system has a Q of about 25 when unloaded and approximately 4 when loaded with a typical load, which again is a significant improvement over more conventional arrangements.

Figure 10:
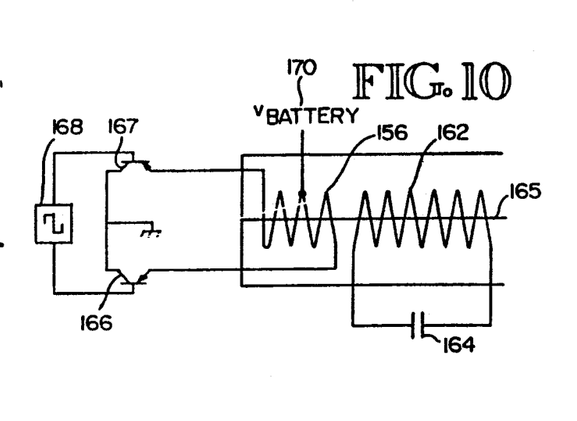
FIG. 10 is a diagram showing a variation of the energy storage feature of FIG. 9.

Another advantage of the primary coil and resonating coil arrangement is the ability to facilitate pulse width modulation of the primary coil drive waveform. Pulse width modulation can be used to efficiently compensate for changing battery and load conditions, and to adjust the supplied power. A single coil drive would normally require a low impedance path constantly applied to the terminals to avoid large voltage spikes; this operation generally complicates the topology of switching transistors. The dual coil drive allows the primary coil to be opened during zero drive intervals, with the secondary ampere-turns adjusting fractionally to absorb the ampere-turns not being supplied by the primary. FIG. 10, which is a modification of the circuit of FIG. 9, shows such a circuit configuration. A center tapped primary coil, with battery 170, permits the use of a drive circuit which includes transistors 166, 167 and an oscillator 168.

Thus, a magnetic drive vibrating toothbrush has been disclosed which is capable of operating in a practical and efficient manner, because of particular structural features and arrangements. Such a vibrating toothbrush is capable not only of scrubbing the teeth but also maintaining cavitation and streaming for a truly acoustic effect.

In one embodiment, the resonating system includes a particular mass and pivot arrangement which results in cavitation and streaming. The lever arm, brush and pivot member are all resonant members with mass and spring constants which result in a natural mode of resonance of the mechanical system at the desired frequency for effective tooth cleaning action, including a scrubbing action and cavitation and streaming effects. The operating frequency of the drive system is selected to be relatively close to the resonant frequency of the mechanical system. The deflection of the brush can be quite high with a minimum amount of electrical energy, due to the reinforcement effect relative to the natural resonance of the mechanical system. The torsion arm pivot member, furthermore, permits a relatively simple but reliable design approach for the entire apparatus.

In another embodiment, the operating (drive) frequency is selected to be offset from the unloaded resonance frequency. At the operating frequency the properties of the vibrating structure are modified by the loading of the brush so that the amplitude of vibration increases with load, as shown in FIG. 2. This is a significant and unexpected result which significantly improves the operation of the toothbrush.

It should be understood that the particular magnetic drive and lever arm arrangements disclosed can be utilized for other appliances, including, for example a razor, scissors, various surgical tools, a blender and perhaps even airless sprayers as well as other devices. The present invention is particularly useful when a relatively high frequency of vibration is important in combination with the need for high efficiency. It should also be understood that, in particular, the arrangement of a resonance coil and a storage capacitor in combination with a primary coil, in order to store reactive energy, may be used in a variety of appliances to improve efficiency.

Although various embodiments of the invention have been disclosed for illustration, it should be further understood that various changes, modifications and substitutions may be incorporated in the embodiments shown without departing from the spirit of the invention which is defined by the claims which follow:

What is claimed is:

1. A vibrating toothbrush, having a magnetic driver, comprising:
    a toothbrush body;
    a lever arm having toothbrush bristles at one end thereof;
    means for mounting the lever arm for vibrating action; and
    an electromagnetic means for driving the lever arm about said mounting means, including permanent magnet means located on said lever arm in the vicinity of the other end thereof, and further including an electromagnet, wherein the electromagnet includes a first inductance to which a driving signal is applied and an energy recovery circuit for storing reactive energy which comprises a series connection of a second inductance and a capacitor, wherein the first and second inductances are arranged such that energy from the first inductance produced by application thereto of the driving signal is coupled into the second inductance, and wherein the second inductance and the electromagnet cooperate with the permanent magnet means to drive said lever arm.

2. An apparatus of claim 1, wherein the mounting means is located in the vicinity of the other end of the lever arm.

3. An apparatus of claim 1, wherein the second inductance has a substantially larger number of turns than the first inductance.

4. An apparatus of claim 1, wherein the electromagnet includes an E-core having top, bottom and center legs and wherein the first and second inductances are coils which are wrapped on the center leg of said E-core such that there is substantially mutual coupling of magnetic flux between the two coils.

5. An apparatus of claim 1, wherein the resonant frequency of the combination of the second inductance and the capacitor is near the frequency of the driving signal.

6. An apparatus of claim 1, wherein the operating frequency is in the range of 150–400 Hz.

7. An apparatus of claim 1, wherein the mounting means includes means tending to maintain the lever arm in a center position between the two extremes of its vibrating action.

8. An apparatus of claim 7, wherein the mounting means includes a spring member connected between the lever arm and the toothbrush body.

9. An apparatus of claim 7, wherein the mounting means includes a torsion assembly including torsion arm means fixedly connected to the lever arm and the toothbrush body, such that when the lever arm is moved in one plane by action of the driving means, movement of the lever arm in orthogonal planes is prevented.

10. An apparatus of claim 1, wherein the toothbrush body is configured to substantially surround the lever arm, thereby substantially preventing contact between the user and the lever arm.

11. An apparatus of claim 1, wherein the lever arm and the mounting means are removable from the toothbrush body, thereby permitting convenient replacement of the lever arm and mounting means.

12. An apparatus of claim 1, wherein the lever arm and the mounting means comprise an integral unit.

13. An apparatus of claim 1, including a fluid-tight sealing member connected to the toothbrush body, located between the permanent magnet and the electromagnet, wherein electromagnetic energy is coupled through the sealing element to the lever arm.

14. An apparatus of claim 1, including a fluid-tight sealing element which extends between the toothbrush body and the lever arm, located in the vicinity of the mounting means.

15. An apparatus of claim 1, including a fluid-tight sealing element located in the vicinity of the one end of the lever arm adjacent the toothbrush bristles.

16. An appliance having a vibrating lever arm, using a magnetic driver, comprising;

an appliance body;

a lever arm having an operating element at one end thereof;

means for mounting the lever arm for vibrating action; and electromagnetic means for driving the lever arm about said mounting means, including permanent magnet means located on said lever arm in the vicinity of the other end thereof and further including an electromagnet, wherein the electromagnet includes a first inductance to which a driving signal is applied and an energy recovery circuit for storing reactive energy which comprises a series connection of a second inductance and a capacitor, wherein the first and second inductances are arranged such that energy from the first inductance produced by application thereto of the driving signal is coupled into the second inductance, and wherein the second inductance and the electromagnet cooperate with the permanent magnet means to drive said lever arm.

17. An apparatus of claim 16, wherein the mounting means is located in the vicinity of the other end of the lever arm.

18. An apparatus of claim 16, wherein the second inductance has a substantially larger number of turns than the first inductance.

19. An apparatus of claim 16, wherein the electromagnet includes an E-core comprising top, lower and center legs, and wherein the first and second inductances are coils which are wrapped on the center leg of said E-core such that there is substantial mutual coupling of magnetic flux between the two coils.

20. An apparatus of claim 16 wherein the resonant frequency of the combination of the second inductance and the capacitor is near the frequency of the driving signal.

* * * * *